United States Patent [19]

Cunisse et al.

[11] Patent Number: 4,531,839

[45] Date of Patent: Jul. 30, 1985

[54] AUTOMATIC DISPENSER-MIXER

[75] Inventors: Michel Cunisse, Saint-Jean-de l'Union; Patrick Granier, Mazamet, both of France; Antoine D'Hollosy, AAn-de-Vecht, Netherlands; Daniel De Pinho, Toulouse, France

[73] Assignees: Cavex-France, Sarl; Comat, Sarl; Microtec, Sarl, all of France

[21] Appl. No.: 533,375

[22] Filed: Sep. 16, 1983

[30] Foreign Application Priority Data

Sep. 17, 1982 [FR] France .................................. 82 15916

[51] Int. Cl.$^3$ .............................................. B01F 11/00
[52] U.S. Cl. ..................................... 366/110; 222/63; 366/111; 366/128; 366/160; 366/162; 366/602
[58] Field of Search ........................ 366/108, 110–115, 366/116, 127, 128, 141, 142, 151, 152, 154–158, 160, 177, 182, 602; 222/226, 52, 229, 56, 236, 238, 241, 63; 241/170; 310/34

[56] References Cited

U.S. PATENT DOCUMENTS

| 2,458,692 | 1/1949 | Downer | 366/111 |
| 3,347,530 | 10/1967 | Platt | 366/602 X |
| 3,533,601 | 10/1970 | Woodham | 366/602 X |
| 3,920,223 | 11/1975 | Krueger | 366/156 |

Primary Examiner—Timothy F. Simone
Attorney, Agent, or Firm—Jordan B. Bierman

[57] ABSTRACT

An automatic dental amalgam dispenser-mixer comprising a first reservoir for silver powder and a second reservoir for mercury, dispensing and metering means for each material, and a mixer equipped with a recovery cup at its outlet. The dispensing and metering means includes a pair of separate conveyors—one for the silver powder and one for the mercury—each rotationally mounted in a sleeve having an inlet in communication with the associated reservoir and an outlet leading to the mixer. The rotational movement of each of the conveyors is separately controlled through stepping motors. An electronic control unit has a stored program for controlling the actuation of each of the conveyors and the mixer, and a keyboard and display for entry of the parameters of the desired mixture.

18 Claims, 9 Drawing Figures

AUTOMATIC DISPENSER-MIXER

This application claims the priority of French Application No. 82.15916, filed on Sept. 17, 1982.

FIELD OF THE INVENTION

The present invention concerns an apparatus for the automatic, programmed dispensing and mixing of materials and, in particular, of constituents for a silver-powder-based dental amalgam.

Conventional apparatus, called a "dispenser-mixer" in the context of the present invention, typically has a tank for the mercury and a tank for the silver powder, with an opening at the lower part leading through metering and dispensing means into a mixer equipped with a recovery cup at its outlet. However, known devices of this kind are usually not capable of the accuracy necessary to produce the desired compositions of the finished product. In effect, the metering of the two components required for the amalgam is generally handled by one and the same device. Taking into consideration the fact that the physical properties of the two components are very different (one being a liquid metal and the other a powdered metal), it can be understood that a single device cannot deliver, with appropriate precision, the desired quantities of mercury and silver powder.

French Pat. No. 2,227,850 shows and describes such a unit, in which the device employed for metering the dental amalgam components is in the form of a rotary-mounted cylinder, and embodies lengthwise two spaces, one for the mercury and the other for the silver powder. Using this apparatus, it is difficult to program a different percentage of one of the components, because this percentage is fixed in a ratio proportional to the volumes defined by the two spaces.

SUMMARY OF THE INVENTION

In accordance with the invention, a dental amalgam dispenser-mixer is provided which remedies the aforementioned disadvantages, and which can handle an automatic and continuous series of metering and mixing operations. The apparatus has a reservoir for the mercury and another reservoir for the silver powder. These reservoirs are open at their lower ends and lead through separate product-metering and dispensing means, into a mixer which is equipped with a recovery cup at its outlet. The dispenser-mixer is characterized by the dispensing and metering means having two separate conveyors (one for the silver powder and one for the mercury) rotary-mounted within sleeves and equipped lengthwise with separate intakes and outlets for the silver powder and mercury, respectively. The rotational movement for each of these conveyors is provided by a stepping motor.

This arrangement allows, on the one hand, the use of a different structure for each of the two conveyors and, on the other hand, the provision of different measured quantities for each of the amalgam components. Preferably, the silver powder conveyor is a screw conveyor. A preferred embodiment of the mercury conveyor is a small piston in a cylinder equipped peripherally with at least one calibrated notch, preferably in the shape of a flat notch on the piston. This notch shape allows for minimizing the adhesion of the mercury to the walls of the notch, thereby allowing the droplet of mercury to fall through the force of gravity.

According to one advantageous feature of the invention, the mixer is subjected to vibrations by means of a vibrator having an inclined shaft, one end of which is disposed in the mixer and the other coupled, eccentrically, to a ring propelled by a rotational movement. This arrangement permits, on the one hand, a thorough mixing by the vibrational movements necessary for the brazing of the mixture and, on the other hand, variation of the duration of vibrations in accordance with the rotational actuation of the inclined shaft.

The invention further provides for programming operations of the components of the dispenser-mixer, by means of a central electronic control unit which determines, on the basis of pre-established parameters recorded by the user on a console, the selective starting or actuation of the motors controlling the rotational movements of the two conveyors and the vibrator. The pre-established parameters include the density of the silver powder, the total mass of amalgam to be delivered, the percentage of mercury in the amalgam and the duration of the vibrations. The user of the dispenser-mixer unit may control the parametric data of the program through said console, in order to automatically obtain a dental amalgam that scrupulously adheres to the specified parameters.

DESCRIPTION OF THE DRAWINGS

Although the general aspects of this invention are given above, the further details of the preferred methods and other features of the invention will be better understood by referring to the description below in conjunction with the appended drawings, in which.

DETAILED DESCRIPTION OF THE INVENTION

Figure 1:
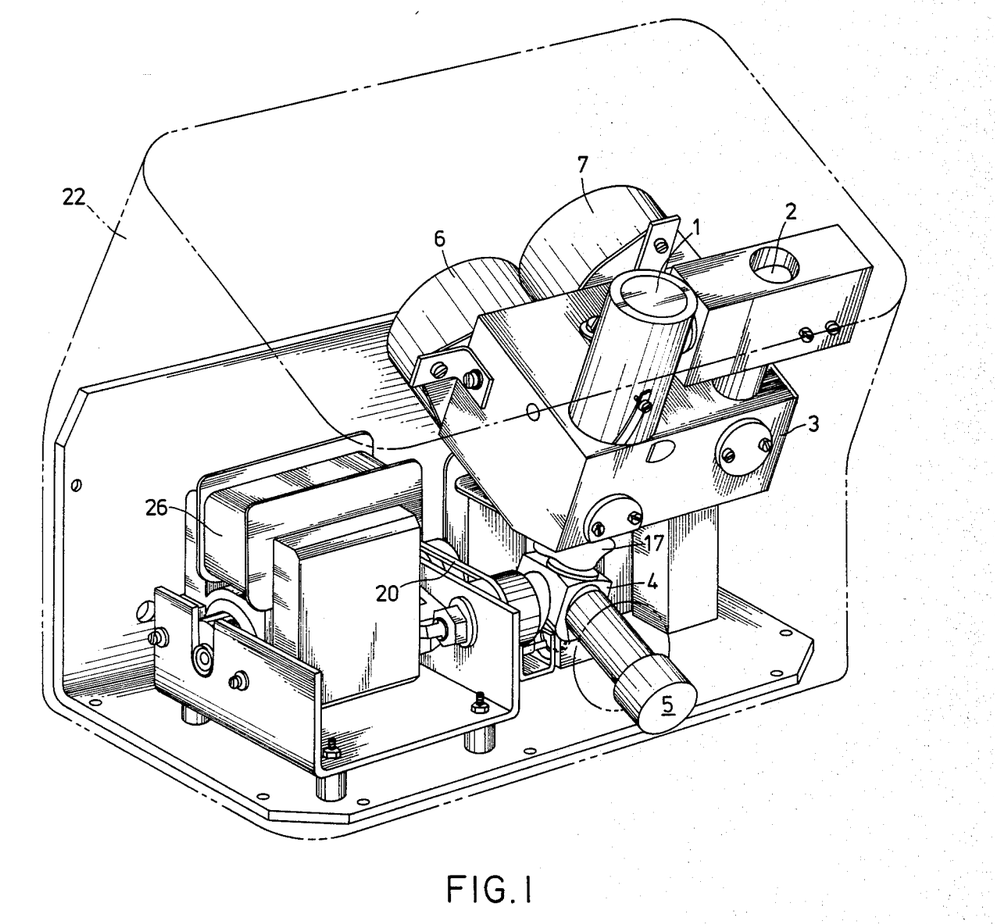
FIG. 1 is a perspective view showing the interior of a dispenser-mixer according to the invention.

The automatic dental amalgam dispenser-mixer shown in FIG. 1 has reservoir 1 for the silver powder and reservoir 2 for the mercury. These two reservoirs are open at the bottom (referenced as 1a and 2a in FIGS. 2 and 3) and lead into dispensing and metering means within housing 3. The dispensed materials pass through mixer 4 to its outlet and recovery cup 5 for the metered and mixed dental amalgam.

Figure 5:
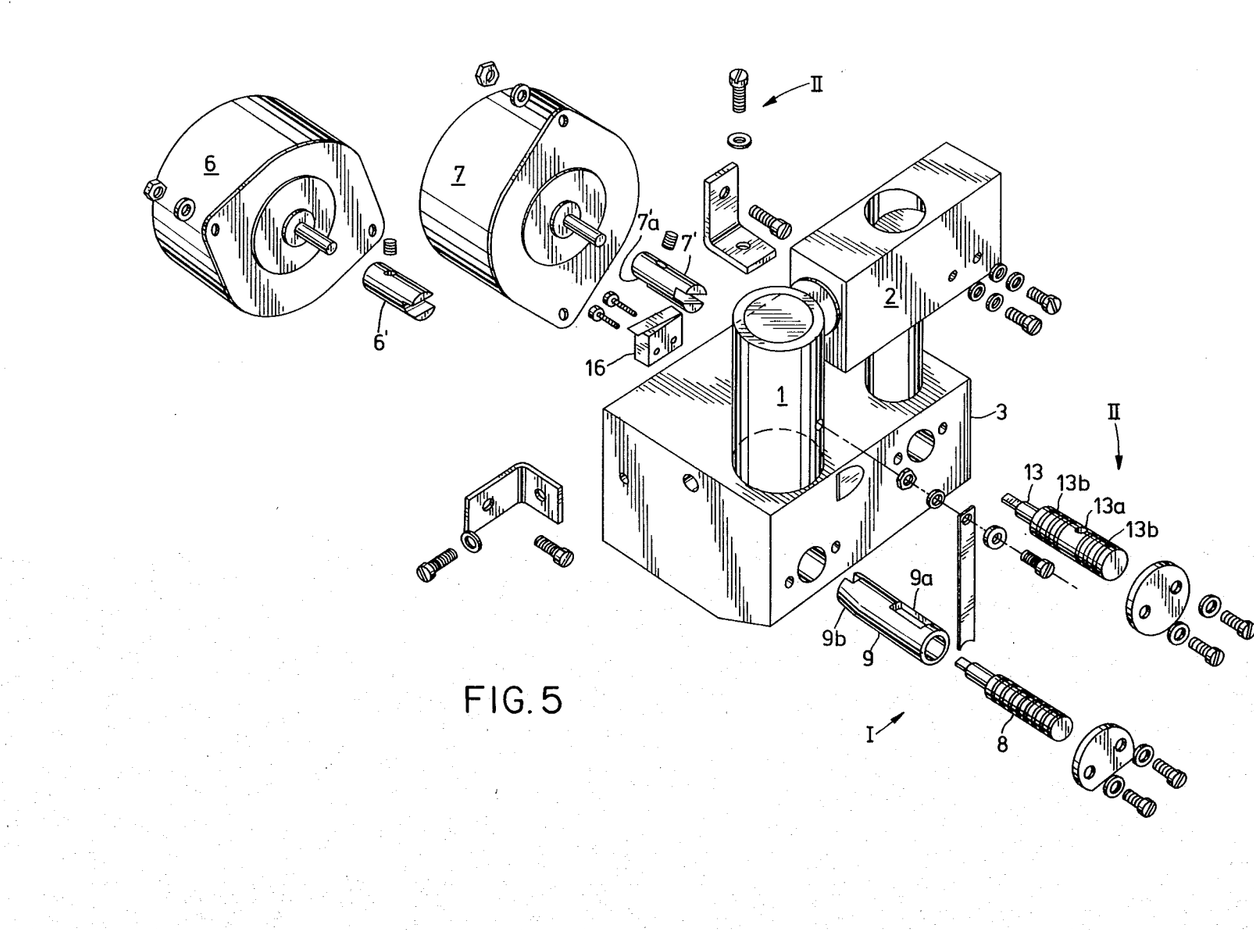
FIG. 5 is a perspective view of the components of the dispensing and metering unit for the apparatus of FIG. 1.

The dispensing and metering means for the materials stored in reservoirs 1 and 2 include a pair of separate conveyors in housing 3, each actuated by rotational movement transmitted by stepping motors 6 and 7 through intermediary couplings 6' and 7', respectively (cf. FIG. 5).

Figure 2:
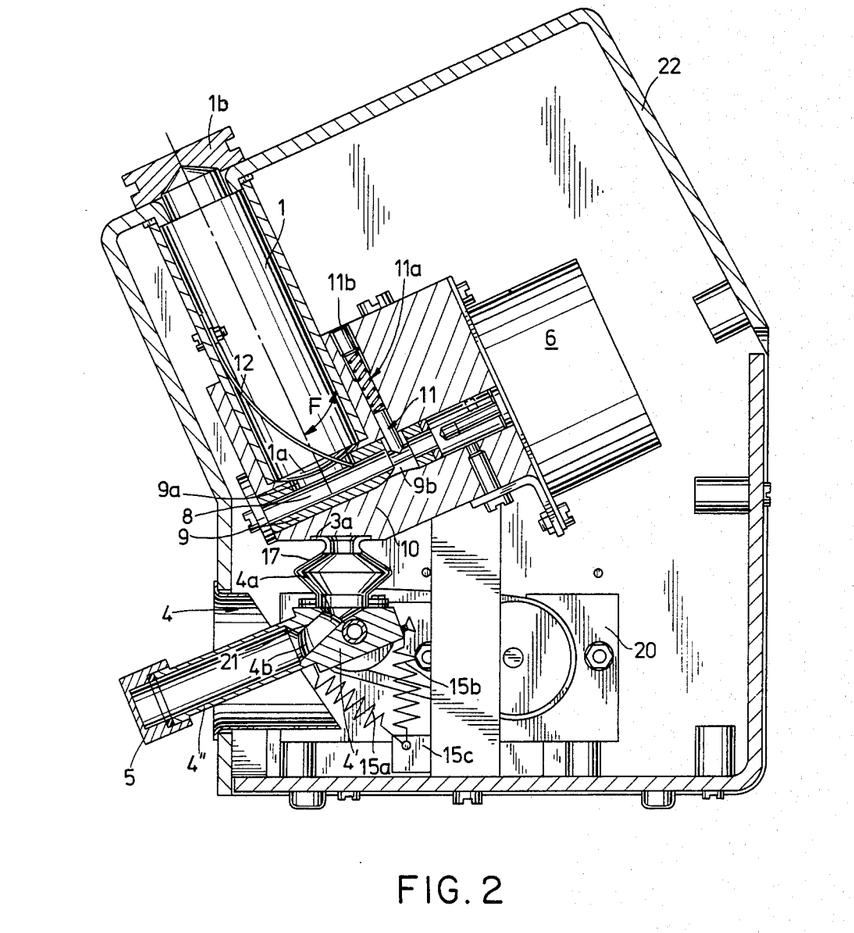
FIG. 2 is a side, sectional view of the apparatus shown in FIG. 1, taken along a vertical plane through the silver powder reservoir.

FIG. 2 illustrates the routing of the silver powder between reservoir 1 and recovery cup 5. According to a preferred embodiment of the invention, silver powder conveyor I, which is shown in greater detail in FIG. 5, is composed of threaded screw 8, rotationally fitted into sleeve 9 and driven by stepping motor 6 and its coupling 6'. Sleeve 9 is equipped with two slots 9a and 9b, the first of which is located opposite opening 1a at the bottom of reservoir 1, and the second is located at the end of the threading of threaded screw 8 leading into short inclined duct 10, which then routes the silver powder to mixer 4. Thus, silver powder stored in reservoir 1 moves downward by gravity through openings 1a and 9a onto the threading of threaded screw 8. The screw, actuated by rotation transmitted by stepping motor 6, carries the powder to the opposite end for dispensing through slot 9b into inclined duct 10. The threading of screw 8 and the number of revolutions will determine—in combination with other parameters—the metered quantities of silver powder.

According to a particularly advantageous feature of the invention, conveyor I for the silver powder cooperates with plunger 11 lodged adjacent the threaded end of threaded screw 8. The plunger 11 is maintained firmly in position by spring 11a on the shaft of threaded screw 8 near the end of the threading opposite slot 9b of sleeve 9. Screw 11b allows for adjusting the tension of spring 11a and, consequently, the intensity of the application force of plunger 11 on the threaded end of screw 8. The purpose of plunger 11 is to dislodge the packed material at the end of threaded screw 8 and to cause all of the powder to fall into slot 9b. This packed material might otherwise accumulate at the aforementioned end of screw 8 and result in inaccurate metering of the powder.

According to another particularly advantageous feature of the invention, silver powder reservoir 1 is equipped with plate-spring 12, the upper end of which is affixed to the inside wall of the reservoir and the lower end being free and resting on the threading of threaded screw 8. Thus, this plate-spring is moved by an oscillating back-and-forth movement (double-direction arrow F), under the rotating effect of the threads of threaded screw 8. When screw 8 is rotated, the resulting movement of plate-spring 12 loosens the silver powder within reservoir 1 so that it can be dispensed through opening 1a.

Figure 3:
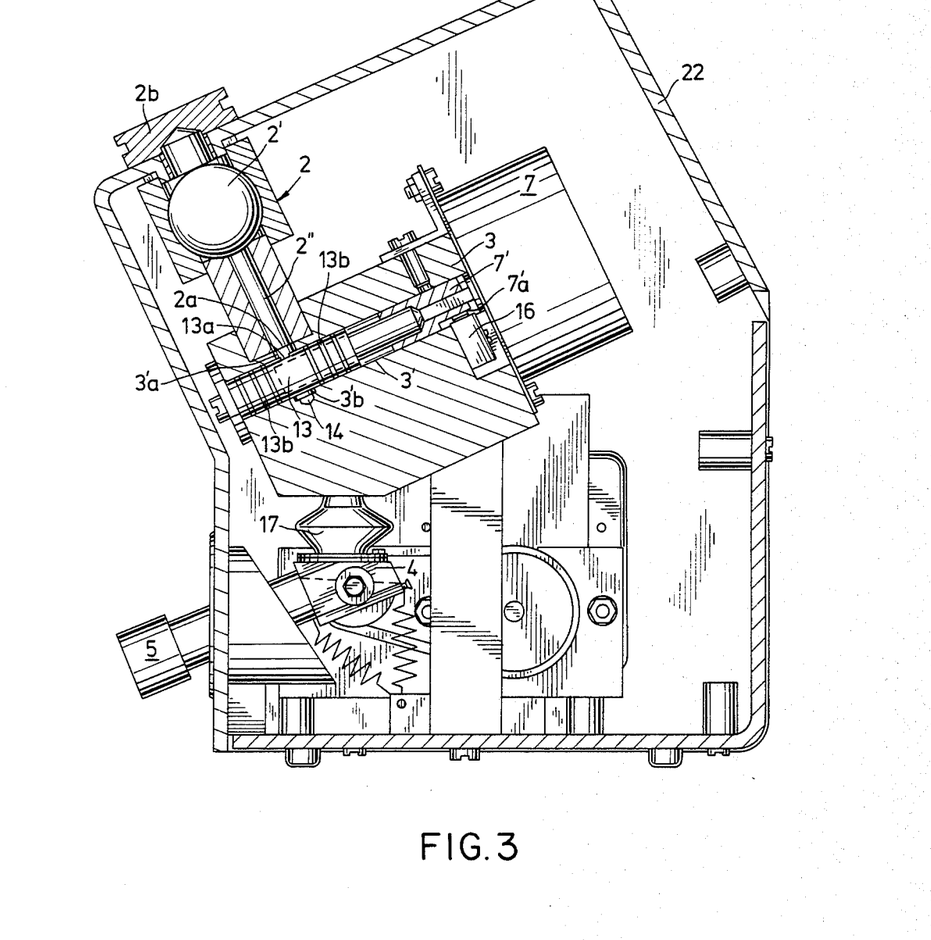
FIG. 3 is a side, sectional view of the apparatus shown in FIG. 1, taken along a vertical plane through the mercury reservoirs.
Figure 4:
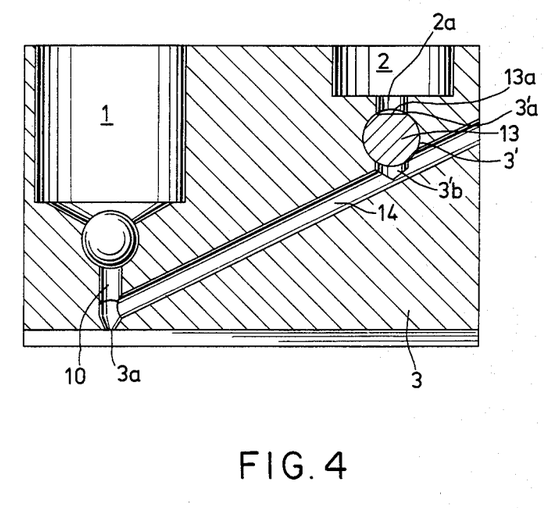
FIG. 4 is a front, sectional cut-away view of the housing of the dispenser-mixer of FIG. 1, taken along a plane through the two reservoir.

FIG. 3 illustrates the routing of the mercury between its storage reservoir 2 and mixer 4. According to a preferred embodiment of the invention, the mercury conveyor II, shown in greater detail in FIG. 5, is composed of a rod or piston 13 equipped on its periphery with notch 13a. Piston 13 is caused to rotate by stepping motor 7 and coupling 7' within sleeve 3' in housing 3, as shown in FIG. 4. The sleeve is equipped with two orifices, one being inlet port 3'a located opposite the bottom opening 2a of reservoir 2, and the other being outlet port 3'b located at the entry to long inclined duct 14. Duct 14 joins at its other end short inclined duct 10 routing the silver powder. Thus, when notch 13a of piston 13 is opposite opening 2a of reservoir 2, the mercury flows into the notch and fills it. Upon rotation of piston 13, notch 13a unloads the mercury through outlet 3'b into duct 14.

Figure 7A:
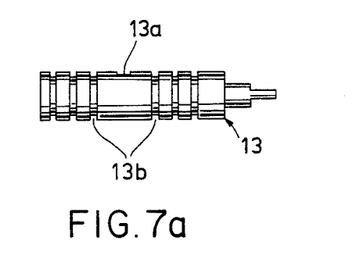
FIGS. 7a and 7b are side and front views, respectively, of components of the dispensing and metering unit shown in FIG. 5.
Figure 7B:
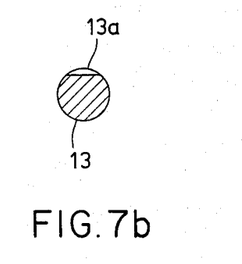

According to a preferred embodiment of the invention illustrated in FIG. 7, notch 13a of piston 13 has a rectangular or flat shape, selected for a weak adhesion of the mercury to it, and for easy machining by simple cutting. This configuration is suitable for delivering small quantities of mercury. Tests on other configurations of notch 13a, for example, a semi-spherical or conical form, showed that, when the notch was opposite duct 14, the mercury droplet did not flow because it conformed to the semi-spherical or conical walls. The resulting adhesion forces were greater than the gravitational force which would make the droplet fall.

According to another preferred embodiment of the invention in FIG. 3, mercury reservoir 2, at its top part 2', has an enlarged volume. The result of this arrangement is to maintain in narrow column 2", below storage volume 2', sufficient pressure for ensuring a regular flow of mercury to notch 13a.

In a further advantageous feature of the invention, coupling 7' connecting piston 13 to its drive motor 7 is equipped at one end with step 7'a, which serving as reference point for locating notch 13a to the desired angular position. Step 7'a makes contact with a member of electric switch 16 for controlling the actuation of stepping motor 7 so that notch 13a is always positioned in the same place at the end of each metering operation.

It may also be noted in FIGS. 5 and 7 that peripheral grooves 13b are provided on piston 13, in order to create differential pressures relieving the tightness of piston 13 in its sleeve 3', which tightness is due to the close fit between elements 13 and 3'.

Figure 6:
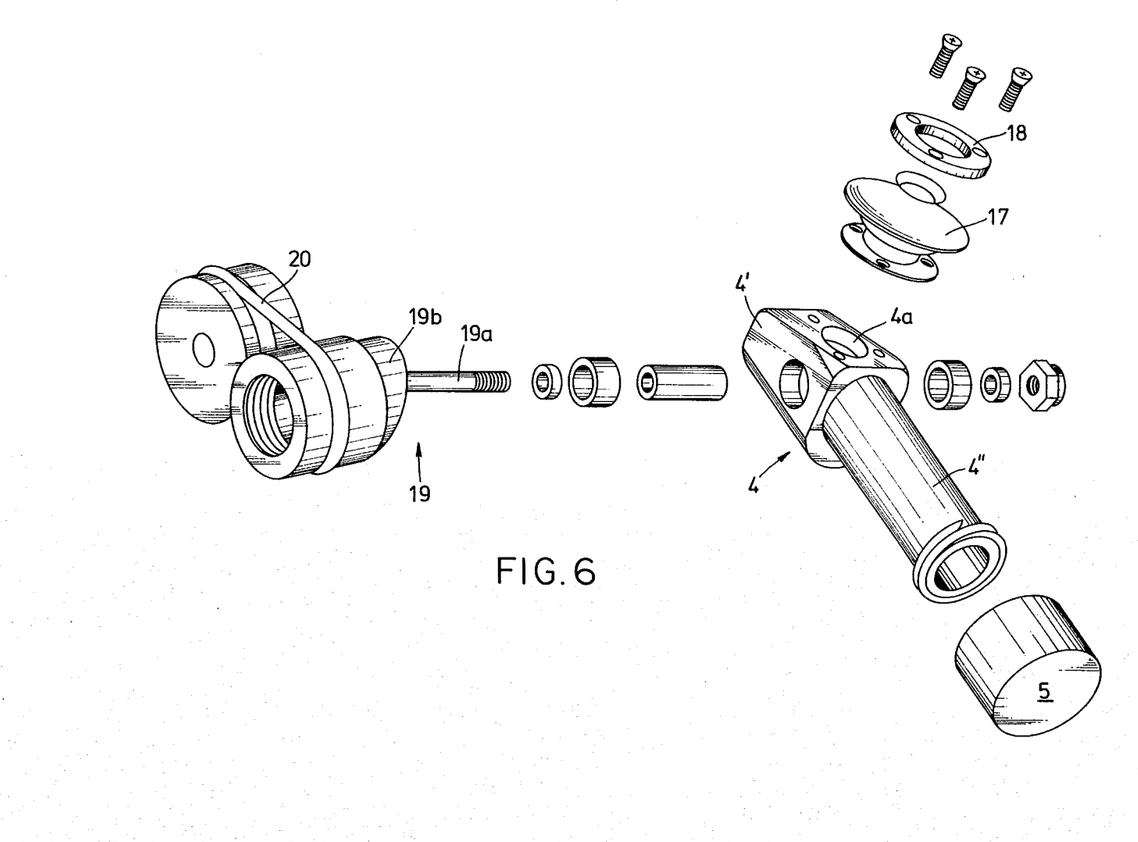
FIG. 6 is a perspective view of the mixer unit in accordance with the invention.

When the silver powder and the mercury have been metered respectively by threaded screw 8 and piston 13, the two products are guided by inclined ducts 10 and 14 as seen in FIGS. 2 and 3, into inlet orifice 4a of mixer 4 through soft, pliable connector 17, preferably having the shape of a bellows. The latter advantageously allows for a flexible connection between outlet 3a from housing 3 (cf. FIG. 2), and inlet 4a of mixer 4, by appropriate fastening means 18 (cf. FIG. 6).

According to a particularly advantageous feature of the invention, mixer 4 is subjected in its entirety to vibrations by means of vibrator 19, having an inclined shaft 19a. One end of shaft 19a is disposed within mixer 4 and the other end is associated, eccentrically, with ring 19b, driven in rotation by a belt connected to motor 20. The connector 17 ensures flexibility between mixer 4, which is movable due to the vibrations of vibrator 19, and housing 3 (containing conveyors I and II), which is stationary.

In a preferred feature of the invention, the equilibrium of mixer 4 around shaft 19a is ensured by the presence of two springs 15a and 15b (cf. FIG. 2), between mixer 4 and movable element 15c, permitting the adjustment of the position of the mixer with respect to vibrator 19.

Mixer 4 has junction box 4', equipped with inlet 4a, an intermediate duct 21 (cf. FIG. 2) and outlet 4b. The outlet 4b leads into duct 4" which is provided at its other end with threading for securing the aforementioned recovery cup 5 for the dental amalgam. Mixer 4 also has a recess for receiving the end of inclined shaft 19a such that eccentric rotation of the shaft results in vibration of the junction box 4' and duct 4". By this arrangement, the silver powder and mercury is guided from connector 17, is thoroughly mixed, and then passed to recovery cup 5.

The different components necessary for the operation of the dispenser-mixer according to the invention have been represented and described above in their most basic form, it being within the capability of a technician to provide various accessory components such as bushings, securing rings, fastening means, etc. The same applies to the installation of the different components, which can be arranged differently without in any way changing the basic concepts of the invention.

The operation of the dispenser-mixer will now be described. Reservoirs 1 and 2 are filled with silver powder and mercury, respectively. Preferably, these reservoirs are inclined for facilitating the filling, and equipped with covers designated 1*b* and 2*b*, respectively. The silver powder drops through opening 1*a* of its reservoir and opening 9*a* of sleeve 9 into the grooves of the threads of threaded screw 8. The mercury, on the other hand, flows via opening 2*a* of its reservoir and inlet 3'*a* of sleeve 3', into notch 13*a* of piston 13. Motors 6 and 7 for each conveyor are actuated separately in accordance with a selected composition of the amalgam. Rotation of threaded screw 8 carries the silver powder to outlet 9*b* of sleeve 9, and rotation of piston 13 moves a mercury droplet received in notch 13*a* over outlet 3'*b*. The metered amounts of silver powder and mercury are then routed through duct 10 (for the silver powder) and duct 14 (for the mercury) towards outlet 3*a* of housing 3. The mixture passes successively though bellows connector 17, duct 21, and duct 4" into recovery cup 5. Upon completion of the desired amount of time for vibration, motor 20 is shut off, and the user can then unscrew recovery cup 5 and recover the dental amalgam deposited there.

Figure 8:
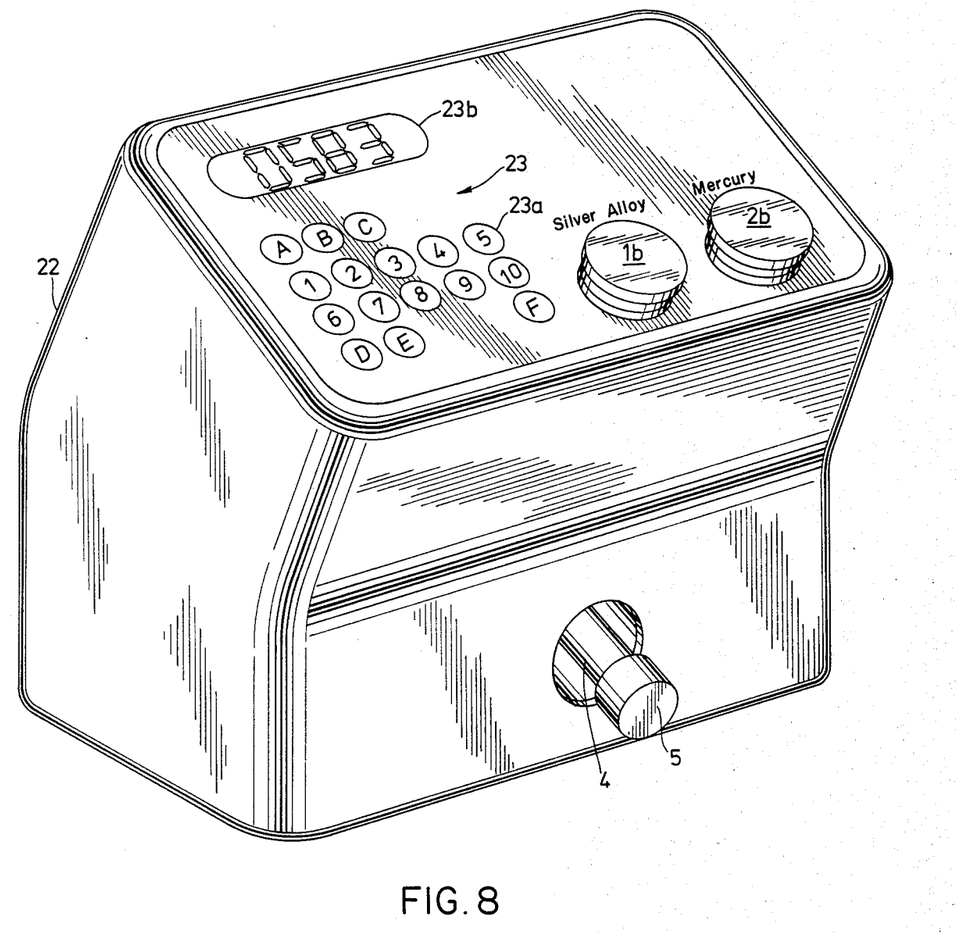
FIG. 8 is a perspective view showing the outside of the dispenser-mixer of FIGS. 1 to 7.

Referring to FIG. 8, the coordination of the operations of the different components mentioned above is provided by a control device housed within module 22, which likewise serves as a protective casing for all of the components of the dispenser-mixer. The control device is composed of a central electronic unit which determines, on the basis of a pre-established program, the selective actuation of motors 6, 7 and 20, and therefore the rotation of threaded screw 8, piston 13 and vibrator ring 19*b*. This pre-established program includes, more notably, stored commands for executing the operations in accordance with the desired amalgam parameters. Stored parameters may include, for example, the pitch of threaded screw 8, number of revolutions of threaded screw 8 for given quantities of silver powder, volume of notch 13*a*, number of revolutions of piston 13 for given quantities of mercury, etc. Input parameters to be provided by the user may include the density of the silver powder used, the total mass of the dental amalgam to be delivered, the percentage of mercury in said dental amalgam, and the duration of the vibrations. The input parameters for the program are entered through control console 23 mounted on the upper face of module 22.

Control console 23 is composed of keyboard 23*a*, for the manual entry of the parameters, and digital display screen 23*b*, which permits the user to verify the parameters entered on the keyboard. Keyboard 23*a* preferably has six function keys ("qualitative" keys) on which the letters A, B, C, D, E, F appear on a white background, and ten so-called "quantitative" keys, on which the ten decimal numbers appear on a grey background.

The preferred functions of the qualitative keys are enumerated below:

A : Registers the density of the silver powder placed in reservoir 1 (this density varies according to the nature of the powder used);

B : Registers the total mass of the dental amalgam to be delivered into recovery cup 5 (displayed in milligrams on display screen 23*b*);

C : Registers the percentage of mercury that the user wishes to obtain in the mixture;

D : Determines the duration of vibrations to which the mixer 4 and its recovery cup 5 will be subject;

E : Selects a mode for actuating the vibrator whenever a cup containing a measured mixture of mercury and silver powder is placed on mixer 4;

F : Actuates the dispenser-mixer according to the invention.

The use of the dispenser-mixer described and shown above is simplified because the user need only know the functioning of the console's keys and check the filling of reservoirs 1 and 2. Light or sound alarms may also be provided, in conjunction with detection means for determining the levels of silver powder and mercury in reservoirs 1 and 2, to alert the operator to an insufficient level in either of these products. Thus, all the operator needs to do is (1) press key B and one or more of the quantitative keys for registering the total mass of dental amalgam desired; (2) press key C and one or more of the quantitative keys for registering the percentage of mercury desired; (3) press key A and one or more of the quantitative keys for selecting the density of the silver powder to be used; (4) press key D and one or more quantitative keys for ordering the duration of the vibrations; and finally, (5) press key F for triggering the operation of the dispenser-mixer when the parametric data of the mixture have been recorded. When the vibration has been terminated, the user simply releases recovery cup 5 and removes the prepared dental amalgam.

Although this invention is described with reference to the above specific materials, steps, and elements, it shall be understood that a variety of modifications may be made without departing from the principles of the invention. For example, parts may be reversed, sequences of method steps may be modified, and various equivalent materials may be substituted for those specifically shown and described. All such modifications are intended to be included within the spirit and scope of the invention, which is defined in the following claims.

We claim:

1. An automatic dispenser-mixer apparatus comprising: a first reservoir for a first material, a first dispenser opening of said first reservoir, a second reservoir for a second material, a second dispenser opening of said second reservoir, dispensing and metering means including a first sleeve, a first conveyor for said first material, said first conveyor being rotationally mounted in said first sleeve, a second sleeve, and a second conveyor for said second material, each said sleeve having an inlet connected to said first and second openings, respectively, and an outlet for each said material being dispensed and metered, separately controllable driving means for each said conveyor, said second conveyor being a piston having a calibrated notch rotatable within said second sleeve to a position adjacent the second opening, controlling coupling means between said driving means and said piston for locating said notch on said piston relative to the second opening, and means for receiving the metered materials from said outlets and mixing them.

2. The apparatus described in claim 1, wherein said first material is silver powder, and the first conveyor is a threaded screw.

3. The apparatus described in claim 1, wherein said second material is mercury, and the second conveyor is a piston having a calibrated notch rotatable within said sleeve to a position adjacent the opening from said second reservoir.

4. The apparatus described in claim 1, wherein said means for receiving includes a vibrator having an inclined shaft, one end of which is in contact with the means for receiving and the other is eccentrically coupled to a ring adapted for rotation.

5. The apparatus described in claim 2, wherein said threaded screw has a series of threads including an end thread adjacent said outlet, and further comprising a plunger biased in contact with said end thread for dislodging the silver powder through said outlet into said means for receiving.

6. The apparatus described in claim 2, wherein said first reservoir is equipped with powder loosening means comprising a plate spring having one end affixed to an inside wall of the reservoir, and the other end resting upon the threads of the threaded screw, whereby rotational movement of said screw causes an oscillating movement for loosening the powder.

7. The apparatus described in claim 3, wherein the inlet of said sleeve is located adjacent the opening from said second reservoir, and the corresponding outlet is located in said sleeve diametrically opposite said inlet.

8. The apparatus described in claim 3, wherein said notch of said piston has a flat shape.

9. The apparatus described in claim 3, wherein said piston is provided on either side of said notch with at least one peripheral groove.

10. The apparatus described in claim 3, further comprising a switch electrically connected to the driving means for said piston, and a coupling between said driving means and said piston, wherein said coupling has a recess and said switch has an actuating member movable into said recess for controlling the rotation of said coupling and piston so as to locate said notch on said piston adjacent the inlet or outlet of said sleeve.

11. The apparatus described in claim 3, further comprising a soft, pliable connector between said outlets and said means for receiving.

12. The apparatus described in claim 4, further comprising means for adjusting the position of said means for receiving with respect to said inclined shaft.

13. The apparatus described in claim 4, wherein said means for receiving includes a junction box having an opening in communication with said outlets, a recess for receiving said one end of said inclined shaft of the vibrator, an outlet from said junction box, an extended duct in communication with said junction box outlet, said duct having means on the end thereof remote from said junction box for securely retaining a recovery cup thereon.

14. The apparatus described in claim 11, wherein said connector is a bellows.

15. The apparatus described in claim 3, wherein said second reservoir has an upper part of large volume and a lower part in the form of a narrow column.

16. The apparatus described in claim 1, further comprising a control device having a central electronic control unit for controlling the selective actuation of each of said conveyor driving means and the mixing function of said means for receiving in accordance with a pre-established program.

17. The apparatus described in claim 16, wherein said pre-established program comprises stored commands for registering the density of the first material, the total mass of the mixture to be delivered, the percentage of the second material in said mixture, and the duration of actuation of the mixing function.

18. The apparatus described in claim 16, further comprising a keyboard for manual entry of selected parameters into said central electronic unit for the establishment of said program, and a display for displaying the parameters entered on said keyboard.

* * * * *